(12) United States Patent (10) Patent No.: US 6,589,242 B1
Feiler (45) Date of Patent: Jul. 8, 2003

(54) PERCUTANEOUS SCAPHOID FIXATION METHOD AND DEVICE

(76) Inventor: Frederic C. Feiler, 10 Mesa Dr., Colorado Springs, CO (US) 80906

(*) Notice: Subject to any disclaimer, the term of this patent is extended or adjusted under 35 U.S.C. 154(b) by 220 days.

(21) Appl. No.: 09/693,580

(22) Filed: Oct. 20, 2000

(51) Int. Cl.⁷ ............................................. A61B 17/56
(52) U.S. Cl. ......................................... 606/56; 606/96
(58) Field of Search ............................. 606/62, 65, 67, 606/80, 96, 97, 107, 54, 56

(56) References Cited

U.S. PATENT DOCUMENTS 5,429,641 A * 7/1995 Gotfried ...................... 606/67
6,033,407 A * 3/2000 Behrens ........................ 606/62
6,036,696 A * 3/2000 Lambrecht et al. ............ 606/97

FOREIGN PATENT DOCUMENTS

FR      2653987 A1 *   5/1991   ........... A61B/17/60

* cited by examiner

Primary Examiner—Kevin Shaver
Assistant Examiner—Melba Bumgarner
(74) Attorney, Agent, or Firm—Richard W. Hanes; Hanes & Schutz, P.C.

(57) ABSTRACT

A method and apparatus for percutaneous internal fixing of a fractured limb bone including, placing the limb in a stabilizing clamp, demonstrating the fractured bone to be fixed, resolving the course through the fractured bone of an intended fixation device, placing a guide wire through exterior and interior tissue adjacent the fractured bone and along the resolved course and across the fracture faces of the bone, incising the tissue proximate the guide wire, spreading the tissue proximate the guide wire to provide space for a drill bit and a surgical screw in the area surrounding the guide wire, drilling a hole in the bone through the fracture faces by directing a cannulated drill over the guide wire, and installing a cannulated fastening screw within the drilled hole and across the bone fracture site to achieve apposition of the fracture fragments of the bone.

5 Claims, 6 Drawing Sheets

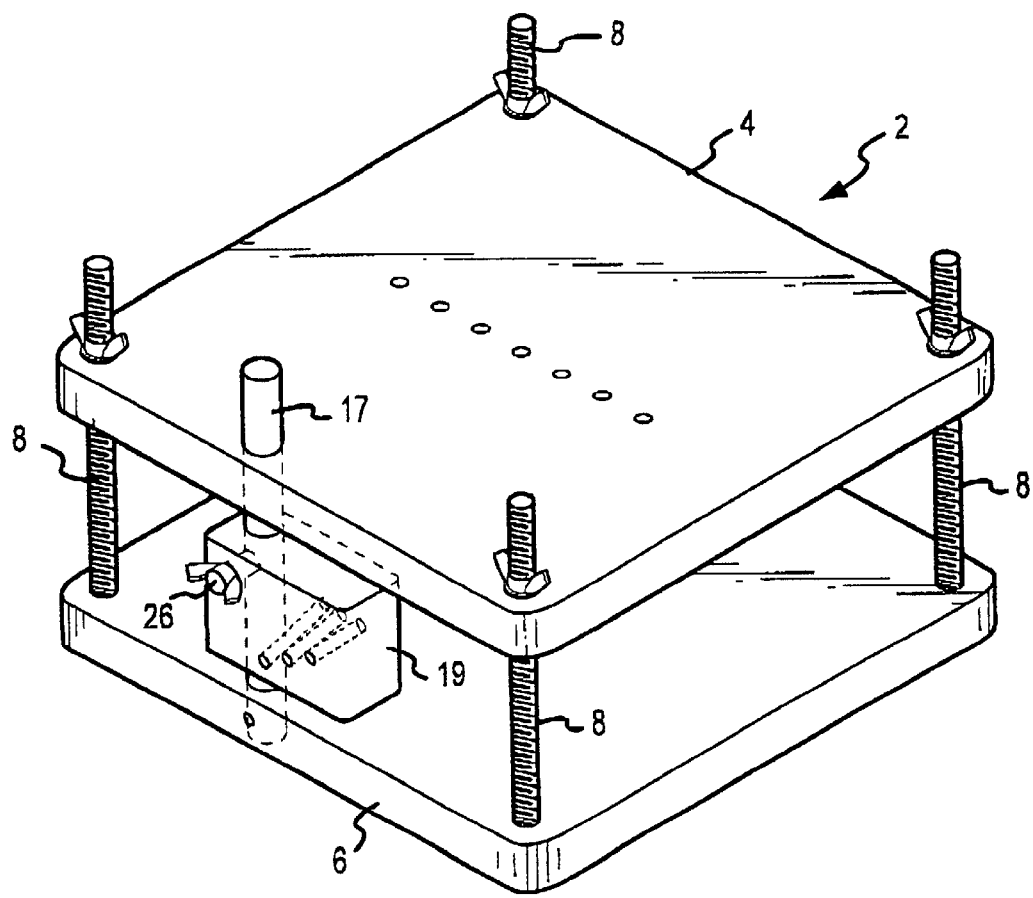
FIG.1
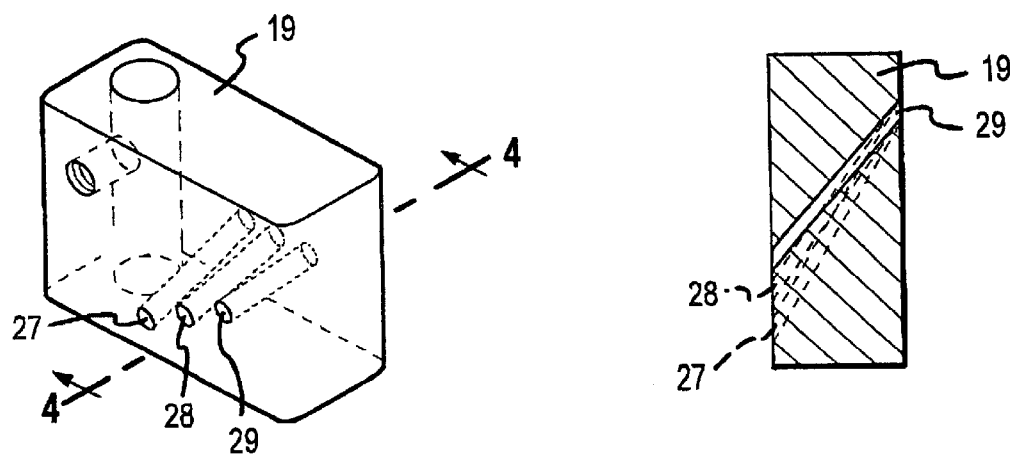
FIG.3
FIG.4

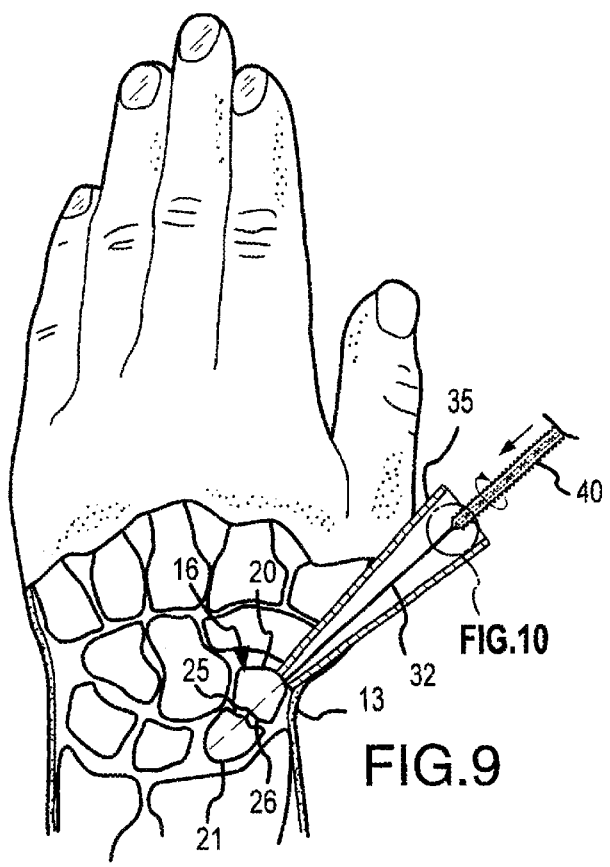
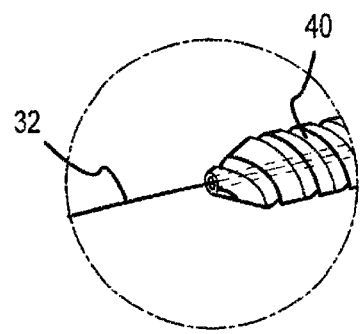
FIG.10
FIG.9
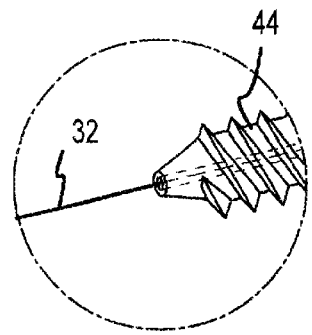
FIG.12
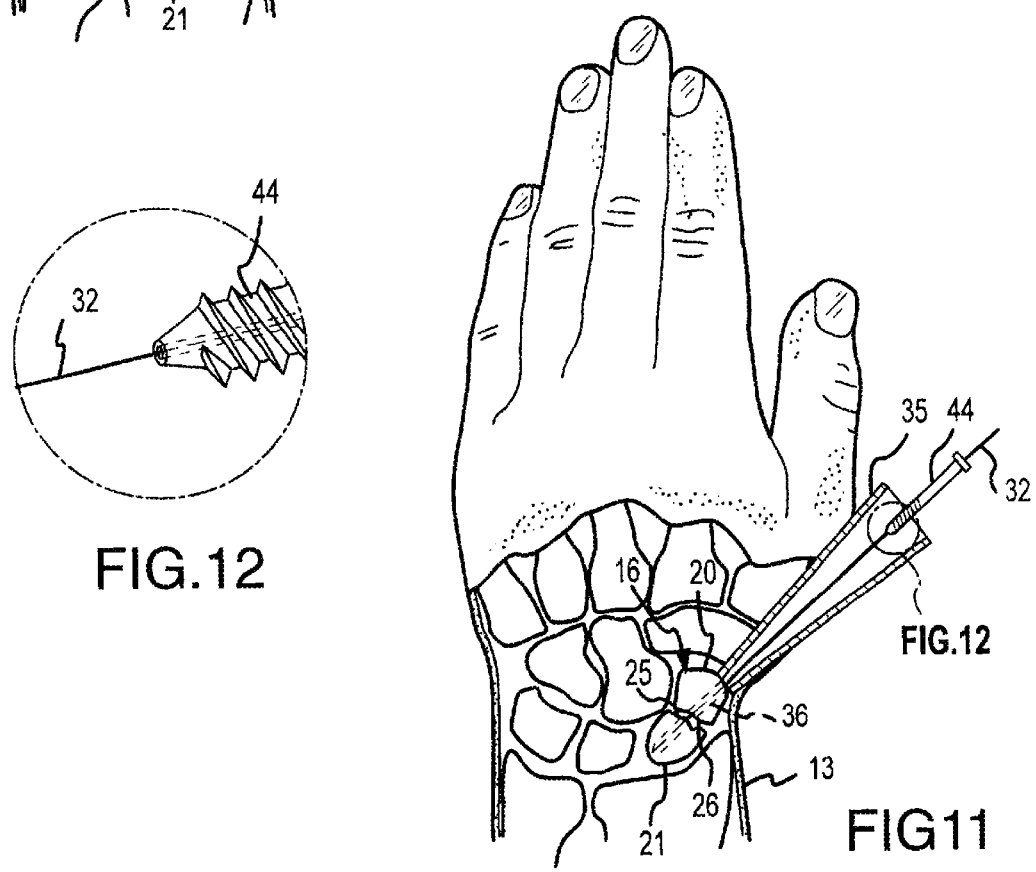
FIG.11

PERCUTANEOUS SCAPHOID FIXATION METHOD AND DEVICE

The present invention relates to surgical methods and devices and in particular to the percutaneous fixation of a fractured scaphoid bone in the human wrist.

BACKGROUND

The boat shaped scaphoid bone in the human wrist is the largest bone of the proximal row of the carpus on the lateral (radial) side, articulating with the radius, lunate, capitate, trapezium, and trapezoid. The scaphoid is surrounded on 80% of its surface by joint fluid containing fibrinolysin, a substance that dissolves blood clots.

The scaphoid is frequently fractured in young adults through the mid-portion, or "waist" of the bone. Because blood clots are necessary for the healing of bone fractures, the substantial presence of fibrinolysin around the scaphoid inhibits healing of a fracture of that bone unless the fracture fragments are fixed in sufficiently good apposition that joint fluid is prevented from entering the fracture site. Failure to properly fix the bone fragments into apposition will result in a non-union because of the presence in the fracture site of joint fluid.

In addition to the undesirable non-union result of poor apposition a fracture of the scaphoid through its waist often leads to avascular necrosis or death of the distal pole of the bone. This is because the blood supply to the bone is chiefly through the proximal pole and an unhealed fracture at the bone waist cuts off the blood supply to the distal pole, resulting eventually in severe arthritis and deformity of the wrist.

The traditional conservative treatment of a fractured scaphoid includes the application of a cast to the hand and thumb with the hand in radial deviation in an effort to oppose the fracture ends of the bone. Surgical intervention to fix the scaphoid bone typically includes the use of a Herbert screw which requires the expertise of a hand surgeon specialist and is a tedious and time consuming exposure of the scaphoid bone.

The percutaneous method and the device of the present invention will allow a less experienced hand surgeon or an orthopedist to fix a scaphoid fracture with a lag screw. Such simplification of the procedure leads to good apposition of the bone fragments and an overall improved result, including the minimization of surgical exposure of the wrist.

SUMMARY OF THE INVENTION

The present invention provides a simple percutaneous method that incorporates a novel appliance to promote the procedure. The essence of the method is to accurately resolve the required course of a fixation device, such as a lag screw, and to be able to implant the device along the desired course.

The scaphoid bone is disposed in the wrist at an angle that is demonstrated in an anterior-posterior X-ray and at another substantial angle, as demonstrated in a lateral X-ray view of the wrist. Accordingly, it is difficult to insert a fixation device that will truly follow the desired course into the scaphoid bone without substantial surgical intervention or without the aid of an alignment jig, such as the one of the present invention. The apparatus of the present invention comprises a clamp into which the wrist containing the fractured scaphoid is inserted. The clamp fixes the wrist in position so that A-P and lateral view X-rays may be taken.

From these X-rays, taken together with radio-opaque alignment markers embedded in the clamp, the desired course of a fixation device may be determined. Resolution of the course includes a determination of the direction and angle of the scaphoid, with respect to the radio-opaque alignment markers, as shown on the A-P view, and measurement of the bone's angulation, as shown on the lateral X-ray view. Once the course is determined, a jig carried by the clamp is positioned at the distal pole of the scaphoid and is adjusted to align a guide wire with the desired course. Using the aligned jig to support and direct the guide wire, the wire is drilled through percutaneous tissue and into the scaphoid bone along the course and at the angle dictated by the aligning jig.

Once the guide wire is drilled into the bone, the wrist is removed from the clamp. A small longitudinal incision is made in the tissue on either side of the guide wire and that tissue is then spread in order to accommodate the bit of a drill and the lag screw that will be inserted into the bone.

A cannulated drill bit is passed over the guide wire and a hole is drilled to terminate near the proximal end of the scaphoid bone. Following removal of the drill, a cannulated lag screw of appropriate length is passed over the guide wire and screwed into the bone, bringing the fracture fragment faces snugly together in good apposition. The spread tissue is allowed to retract, the guide wire is removed and the incision is closed with a few sutures.

The bone apposition achieved by the accurately placed and well fitted lag screw prevents joint fluid from entering the fracture site and dissolving the blood clots that are necessary for bone union.

DESCRIPTION OF THE DRAWINGS

FIG. 1 is a perspective view of the limb clamp of the present invention.

FIG. 3 is a perspective view of the guide wire jig.

FIG. 4 is a cross sectional view taken along lines 4—4 of FIG. 3.

FIG. 9 is a fragmentary posterior view of the wrist with the tissue expander shown in cross section and illustrating a portion of a cannulated drill bit being inserted over the guide wire, which has previously been inserted into the scaphoid bone, shown in dotted lines.

FIG. 10 is an enlarged detail of the tip end of the drill taken within the circle 10 of FIG. 9.

FIG. 11 is a view similar to that of FIG. 9 showing the insertion of a cannular lag screw into the hole in the scaphoid that was created by the drill bit of FIG. 11.

FIG. 12 is an enlarged view of the tip end of the cannular lag screw as it is passed over the guide wire.

DETAILED DESCRIPTION OF THE PREFERRED EMBODIMENT

The bone fracture fixation method and associated apparatus of the present invention are primarily directed toward treatment of a fractured scaphoid bone in the human wrist. However, the invention can be used in the treatment of fractures in other human or animal bones that present the same challenge in determining and following the proper course or angle for the implantation of a fixation device such as a lag screw.

The method and implementing apparatus of the present invention provides a device to secure the limb having the broken bone while X-rays are taken. With the use of the X-rays, the securing, or clamping, device then provides alignment means for the insertion of a wire into the fractured bone that will thereafter guide the course of subsequent procedures, including drilling and the implantation of a fixation device into the fractured bone.

Figure 2:
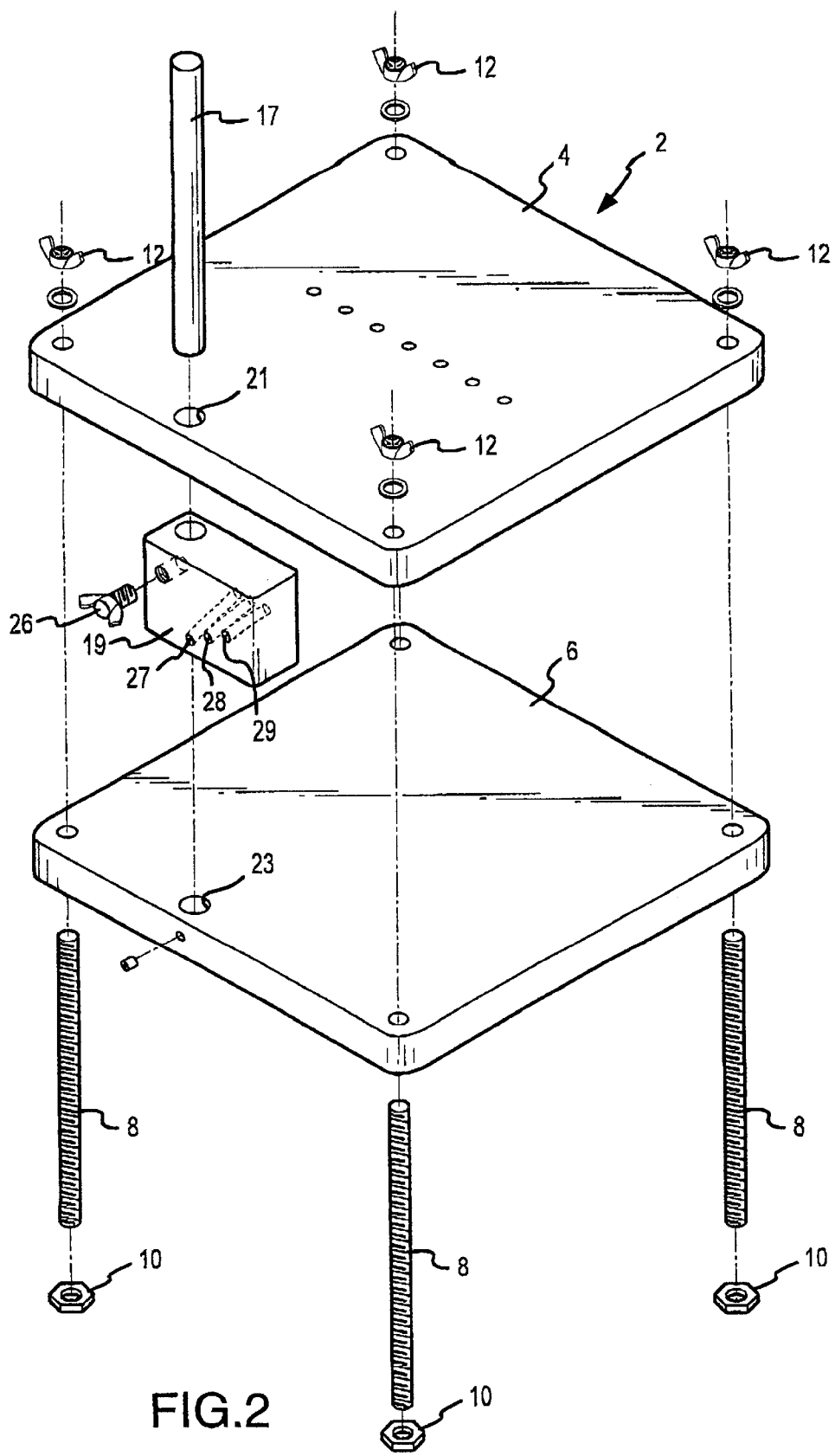
FIG. 2 is an exploded view of the limb clamp.

FIGS. 1, 2, 5 and 6 illustrate a preferred form of the limb clamp 2. Referring to FIGS. 1 and 2, the limb clamp 2 comprises a pair of substantially parallel plates 4 and 6 that are retained in a spaced apart relation with four corner threaded rods 8 and cooperating nuts 10 and hand adjustable wing nuts 12. Although threaded rods and nuts are shown in the preferred embodiment of the invention, other forms of adjustable connectors can be used. Such alternative structures might include ratchet devices, electrical, pneumatic or hydraulically driven adjustable interconnecting linkages. The plates are said to be substantially parallel because in use they appear to be parallel when casually viewed in a clamping position over and under a human wrist 13 (See FIG. 5). However, the adjustment mechanism provided by the threaded rods 8, or their equivalent, permit the plates to be placed in a slightly non-parallel configuration if such a position is necessary to properly secure the particular patient's limb. Each of the plates is of about the same shape as the other, that is the longitudinal and lateral extent of the plates are about the same. If the particular limb being clamped makes it necessary or desirable for the two plates to have different shapes, those diverse shapes would still be within the scope of the invention.

The plates 4 and 6 are constructed from any rigid or semi-rigid material that is transparent to X-ray radiation, such as any number of plastics. One of the plates 4, which can be considered as the top plate, is provided with a plurality of small spaced apart radio-opaque buttons 15 arranged in a straight line. The buttons 15 serve as alignment and aiming markers to be imaged on an anterior-posterior X-ray view of the wrist.

Spaced laterally from the line formed by the alignment buttons 15 is a mounting stand 17 that supports a wire guide alignment jig 19. In the preferred form of the invention the mounting stand is a cylindrical rod 17 whose ends are secured in bores 21 and 23 at the lateral edge of the clamping plates 4 and 6. In the preferred form, the jig 19 comprises a solid block of plastic, metal or wood that is pivotally and slidably mounted on the rod 17. When tightened, the wing nut set screw 26 that is threaded into the side of the jig block 19, serves to lock the jig block in a fixed position relative to the clamping plates 4 and 6. Laterally traversing the jig block are a plurality of holes 27, 28 and 29 that selectively receive a guide wire 32 for the purpose of aligning the wire prior to its being drilled into the scaphoid bone in the wrist that is being retained by the clamping device. The holes 27, 28 and 29 are variously inclined with respect to the plane of clamping plates from about 50° to 60°. This range of angles is exemplary and not to be considered as limiting. The angles of the holes may be whatever is required to substantially align the guide wire with the pertinent axis of the scaphoid bone, considering the bone's inclination with respect to a horizontal plane, as seen in a lateral X-ray view of the wrist.

The novel percutaneous fixation method of the present invention makes use of the clamping device 2 of the present invention. The purpose of the fixation method and the accessory device 2 is to ultimately implant a fixation device, such as a lag screw, accurately across the faces of the fracture fragments so as to achieve maximum apposition of the bone fragments. Snug fitting bone fragments tend to resist the entry of joint fluid into the fracture site, thus eliminating the destruction of the blood clots that are necessary to the union of the bone.

Because the scaphoid bone is relatively small and is disposed in the wrist at a compound angle, it is normally difficult to visualize the position of the bone with sufficient accuracy that a fixation device may be properly implanted across the fracture site. According to the present invention, and assuming a proximal or distal fracture or a fracture through the waist of the scaphoid bone, a guide wire is drilled into the bone along the same course as that desired for the intended fixation device, such as, for example, a lag screw or a bone graft. Once the guide wire is properly in place, the remaining steps of the fixation procedure may proceed, using the guide wire as the pathfinder for subsequent steps of the procedure.

Figure 5:
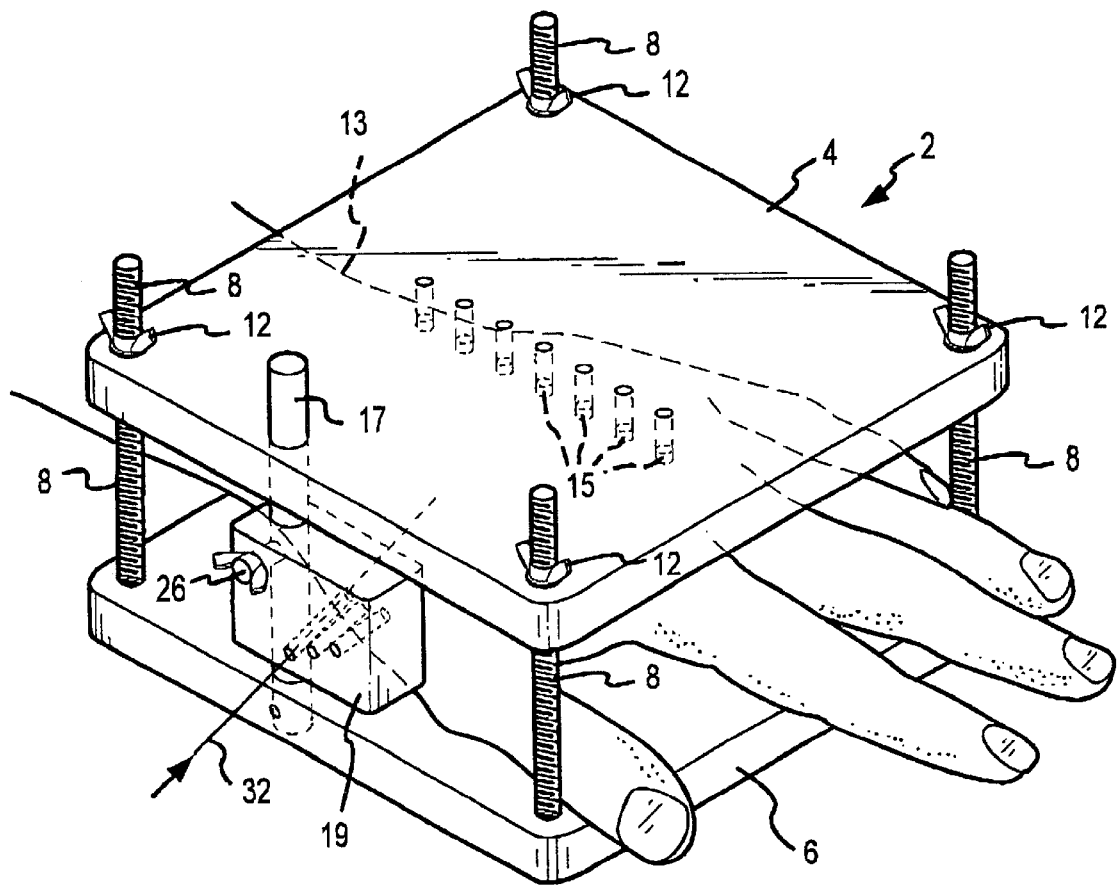
FIG. 5 is a perspective view of the limb clamp with a human hand and wrist in position for X-ray and the placement of a guide wire, in accordance with the novel method of the present invention.

With the patient's wrist 13 secured in the clamping device 2, as shown in FIG. 5, anterior-posterior (AP) and lateral X-rays are taken to demonstrate the position of the scaphoid bone in two planes. The AP view X-ray will, in addition to showing the bones of the wrist, contain a line of spots created by and corresponding to the alignment buttons 15 on the upper plate 4 of the clamp 2. On the AP X-ray, a line may be drawn, or a line may just be visualized, along the desired course of the fixation device from the scaphoid distal pole through the bone fracture site at the point where the fixation device should pass. The line is then extended to pass through or near one of the alignment spots on the X-ray that are created by the radio opaque buttons 15. Thus, the button that created the spot on the X-ray through which the extended line passes, or passes closest to, becomes the aiming target or the alignment point for directing the guide wire in the horizontal plane.

Figure 8:
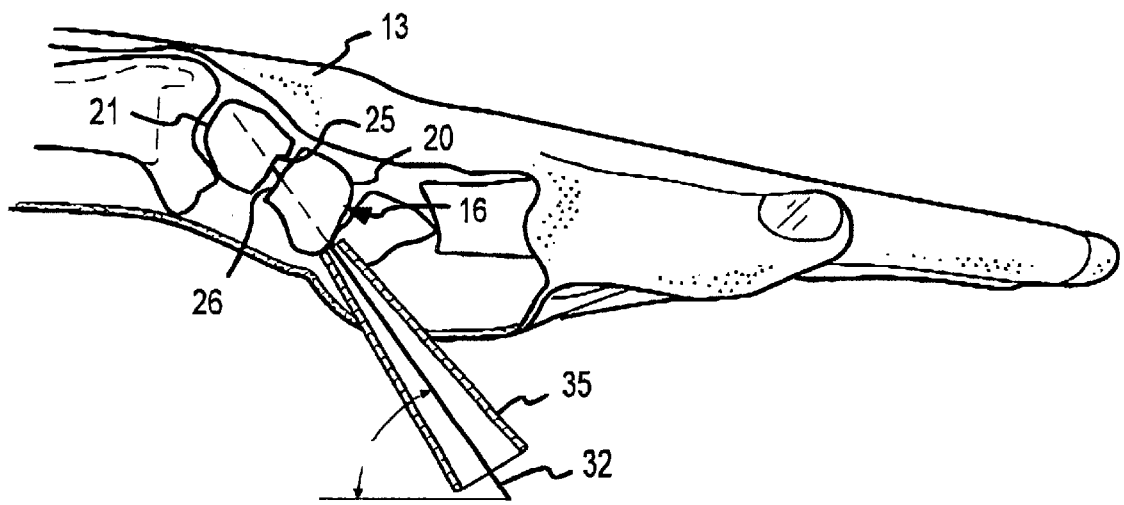
FIG. 8 is a lateral view of the hand and wrist illustrating the insertion into the incision of a tissue expander to make way for a drill bit and a fixation device.

The lateral view X-ray is used to determine the vertical angle from the horizontal of the scaphoid bone, as shown in FIG. 8. When the vertical angle is known, the course of the guide wire in the vertical plane is established. Next, using the measured angle of bone inclination and sighting on a particular one of the buttons 15 on the upper plate 4, the jig block 19 is positioned. The jig is situated vertically with respect to the plates and angularly with respect to the axis of the mounting stand 17 so that one of the plurality of holes 27, 28 or 29 will be aligned with both the horizontal and vertical components of the desired course of the fixation device through the scaphoid bone 16.

Figure 7:
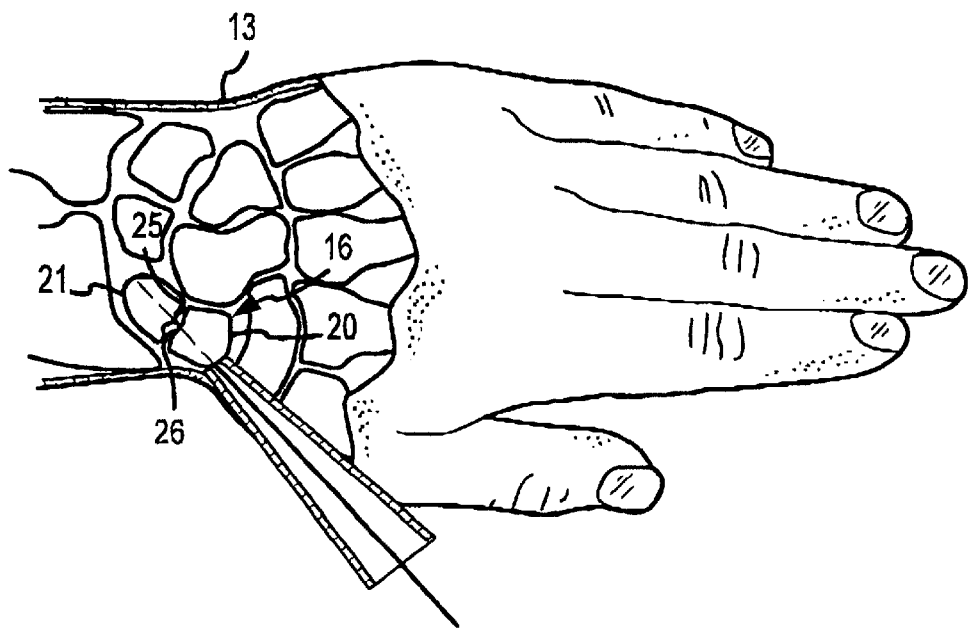
FIG. 7 is a fragmentary posterior view of the hand and wrist following removal of the limb from the clamp and illustrating, in cross section, the presence of a tissue expander inserted into an incision in the skin.

When the alignment is complete and the jig 19 is fixed in its proper position, a guide wire 32 is inserted into the chosen jig hole. The wire is then drilled into the wrist tissue, the volar distal pole 20 of the scaphoid bone and across the fracture faces 25 and 26 to the dorsal proximal pole 21 of the scaphoid, as shown in FIGS. 5, 7 and 8. Once the guide wire 32 is implanted into the scaphoid 16 the unneeded portion of the free end of the wire 32 is clipped off and the alignment jig 19 is pivoted about and/or lowered on the rod 17 so that the guide wire is freed from the jig. The clamping device 2 is loosened and the wrist and hand of the patient is removed therefrom.

Figure 6:
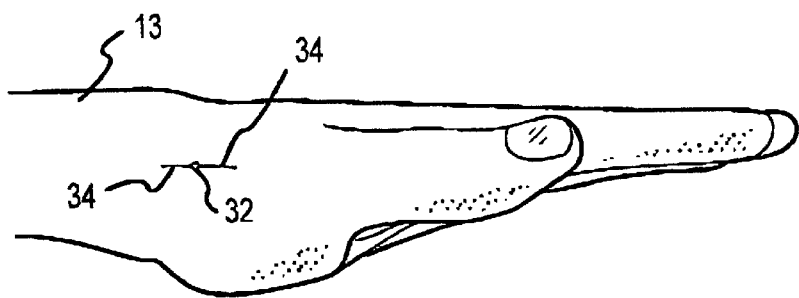
FIG. 6 is a perspective view of the limb clamp with a human hand and wrist in position for the insertion of a guide wire into the scaphoid bone of the wrist, using the jig to properly locate the guide wire.
Figure 13:
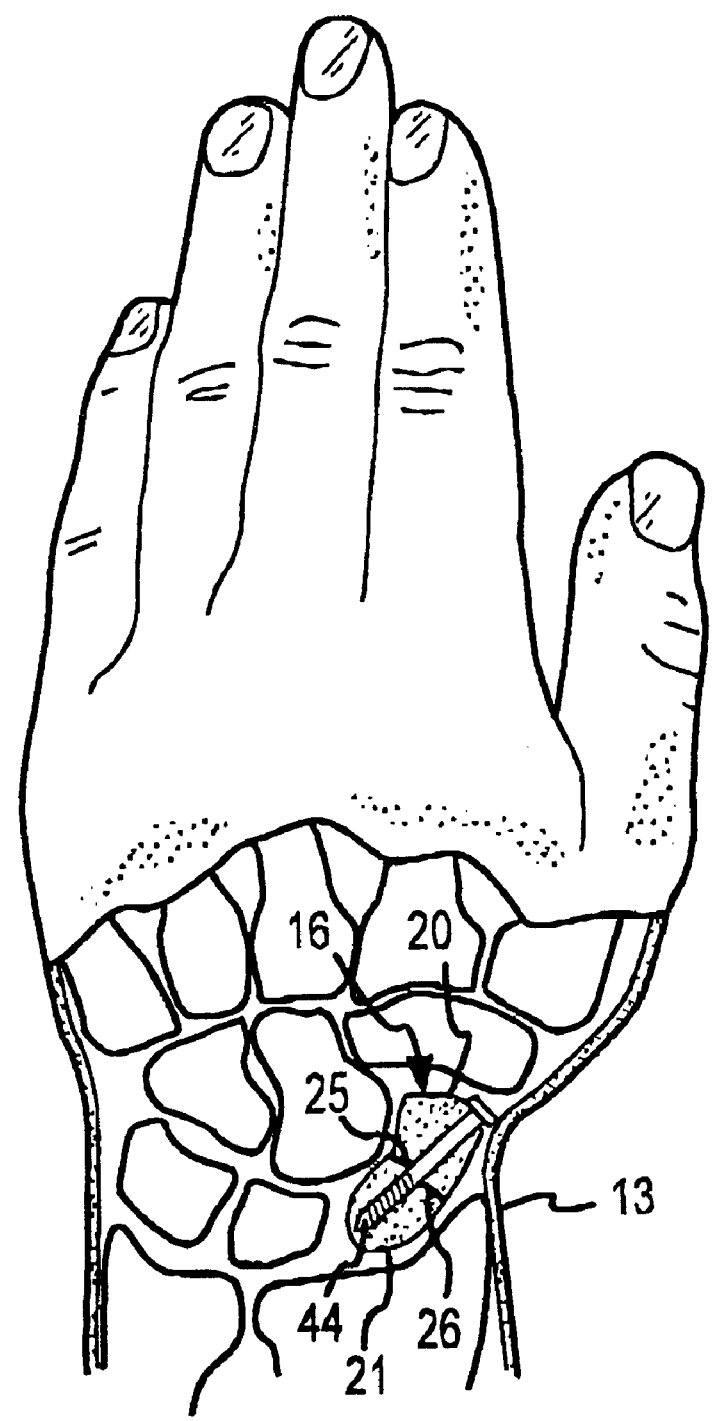
FIG. 13 is a view similar to that of FIG. 11, but illustrating the end result of the process, where the scaphoid bone fragments have been secured in apposition by the fixation device, the lag screw.

A small longitudinal incision 34 is made proximally and distally on either side of the guide wire 32, as illustrated in FIG. 6. As shown in FIGS. 7 and 8, a cone shaped hollow tissue spreader 35 is passed over the guide wire 32 and pressed into the incision 34. The spreader is carefully pushed into the incision until its end impinges on the scaphoid bone. The spreader pushes aside important structures in this area, including the radial artery and its accompanying veins and the terminal sensory branch of the radial nerve that gives sensation to the thumb. Next, as shown in FIGS. 9 and 10 a cannulated drill bit 40 is passed over the guide wire 32 and through the opening prepared in the tissue by the spreader 35. The drill bit 40 follows the guide wire 32 and drills a hole 36 in the scaphoid along the desired course of the fixation device around the guide wire. The hole is of sufficient diameter and length to accommodate a fixation device, such as a lag screw 44. After the drill bit 40 is withdrawn, the cannulated lag screw 44 is passed over the guide wire 32 and screwed into the bone 16, as shown in FIGS. 11, 12 and 13. When the screw has been fully seated and the bone fragments are pulled together in apposition (FIG. 13), the tissue spreader 35 and the wire guide 32 are removed and the small incision 34 is closed with a few sutures.

Employment of the apparatus 2 and the method of the present invention results in good apposition of the bone fragments with reasonable assurance that a union of the fragments will take place, since joint fluid has been isolated from the fracture site.

I claim:

1. A method for percutaneous internally fixing of a fractured bone of a limb including, placing the limb in a stabilizing clamp, demonstrating a fractured bone, having a plurality of fracture fragments with fracture faces, resolving the course of an intended fixation device through the fracture faces of the fractured bone, placing a guide wire through the exterior and interior tissue adjacent the fractured bone along the resolved course and across the fracture faces of the bone, incising the tissue proximate the guide wire;

spreading the tissue proximate the guide wire to provide space for a drill bit and a surgical fixation device in the area surrounding the guide wire, drilling a hole in the fractured bone fragments and through the fracture faces by directing a cannulated drill over the guide wire;

installing a cannulated fixation device within the drilled hole and across the bone fracture faces to achieve apposition of the fracture fragments of the bone.

2. The method of claim 1 where the step of demonstrating the fractured bone to be fixed includes the steps of, demonstrating the anterior-posterior view of the fractured bone, demonstrating the lateral view of the fractured bone, and further including the steps of, measuring the angulation of the scaphoid bone using the lateral view X-ray for vertical orientation of the resolved course, and determining the horizontal orientation of the resolved course by using the anterior-posterior view X-ray.

3. The method of claim 2 and further including the step of extracting the guide wire and closing the tissue incision.

4. The method of claim 1 where the fixation device is a lag screw.

5. A method for percutaneous internally fixing of a fractured bone of a limb including, placing the limb in a stabilizing clamp having an alignment device with at least one bore, demonstrating the fractured bone, having a plurality of fracture fragments with fracture faces, with the aid of the alignment device, resolving the course of an intended fixation device through the fracture faces of the fractured bone, placing a guide wire through the at least one bore of the alignment device and through the exterior and interior tissue proximate the fractured bone along the resolved course and across the fracture faces of the bone, incising the tissue proximate the guide wire;

spreading the tissue proximate the guide wire to provide space for a drill bit and a surgical fixation device in the area surrounding the guide wire, drilling a hole in the fractured bone fragments and through the fracture faces by directing a cannulated drill over the guide wire;

installing a cannulated fixation device within the drilled hole and across the bone fracture faces to achieve apposition of the fracture fragments of the bone.

* * * * *